(12) United States Patent
Trosin et al.

(10) Patent No.: US 9,115,335 B2
(45) Date of Patent: Aug. 25, 2015

(54) PHOSPHORIC ACID ESTERS, THEIR PREPARATION AND USE

(71) Applicant: Evonik Industries AG, Essen (DE)

(72) Inventors: Annika Trosin, Recklinghausen (DE); Sabina Kruczek, Essen (DE); Frank Schubert, Neukirchen-Vluyn (DE); Andre Broetzmann, Essen (DE); Philippe Favresse, Ratingen (DE); Joerg Peggau, Essen (DE)

(73) Assignee: EVONIK INDUSTRIES AG, Essen (DE)

( * ) Notice: Subject to any disclaimer, the term of this patent is extended or adjusted under 35 U.S.C. 154(b) by 0 days.

(21) Appl. No.: 14/216,031

(22) Filed: Mar. 17, 2014

(65) Prior Publication Data

US 2014/0274863 A1 Sep. 18, 2014

(30) Foreign Application Priority Data

Mar. 15, 2013 (DE) .......................... 10 2013 204 605

(51) Int. Cl.
| | | |
|---|---|---|
| *C11D 1/34* | (2006.01) | |
| *C11D 1/78* | (2006.01) | |
| *C11D 3/06* | (2006.01) | |
| *C11D 7/36* | (2006.01) | |
| *C11D 3/36* | (2006.01) | |
| *C07F 9/09* | (2006.01) | |
| *C08J 5/00* | (2006.01) | |
| *G02B 5/00* | (2006.01) | |
| *C07F 9/40* | (2006.01) | |

(52) U.S. Cl.
CPC ................ *C11D 3/362* (2013.01); *C07F 9/094* (2013.01); *C07F 9/4021* (2013.01); *C08J 5/00* (2013.01); *G02B 5/00* (2013.01)

(58) Field of Classification Search
CPC ............ C11D 1/34; C11D 1/345; C11D 1/78; C11D 3/06; C11D 3/362; C11D 7/36; C11D 11/0023
See application file for complete search history.

(56) References Cited

U.S. PATENT DOCUMENTS

| | | |
|---|---|---|
| 6,310,123 B1 | 10/2001 | Boinowitz et al. |
| 6,423,130 B2 | 7/2002 | Boinowitz et al. |
| 6,689,731 B2 * | 2/2004 | Esselborn et al. ............ 510/288 |
| 7,186,675 B2 | 3/2007 | Meine et al. |
| RE39,746 E | 7/2007 | Boinowitz et al. |
| 7,588,647 B2 | 9/2009 | Muller et al. |
| 8,268,939 B2 | 9/2012 | Ebbrecht et al. |

FOREIGN PATENT DOCUMENTS

| | | |
|---|---|---|
| DE | 10054462 B4 | 2/2005 |
| EP | 0940406 B1 | 9/1999 |
| EP | 1167452 A2 | 1/2002 |
| WO | WO9212950 | 8/1992 |
| WO | WO2005026273 A1 | 3/2005 |

* cited by examiner

*Primary Examiner* — Charles Boyer
(74) *Attorney, Agent, or Firm* — Scully, Scott, Murphy & Presser, P.C.

(57) ABSTRACT

The invention relates to phosphoric acid esters of polyether-modified alkyl alcohols, to their preparation and to a use of phosphoric acid esters of polyether-modified alkyl alcohols for generating shine on a surface.

9 Claims, No Drawings

PHOSPHORIC ACID ESTERS, THEIR PREPARATION AND USE

FIELD OF THE INVENTION

The present invention relates to phosphoric acid esters of polyether-modified alkyl alcohols, to their preparation and to a use of phosphoric acid esters of polyether-modified alkyl alcohols for generating shine on a surface.

PRIOR ART

Conventional shine additives for cleaning formulations for hard surfaces are based on additions of wax/acrylic polymers which do not assist cleaning. Such a combination leaves behind a solid film which, firstly, seals the surface and, secondly, can lead to visible tread marks as a result of various mechanical demands. Uneven surfaces are smoothed as a result, and although shine is generated, the surface is also visibly altered in terms of its nature. In most cases, particularly more matt or structured surfaces treated herewith look painted and not freshened up and as new.

EP0940406 describes phosphoric acid esters, which are obtainable by reaction of an ω-hydroxy-functional oligo- or poly(alkyl)styrene with an alkylene oxide to give a poly(alkyl)styrene-block(b)-polyalkylene oxide copolymer and subsequent conversion to the corresponding phosphoric acid esters with a phosphoric-acid-ester-forming phosphorus compound, where up to 100% of the terminal hydroxyl groups of these poly(alkyl)styrene-block(b)-polyalkylene oxide copolymers are converted to phosphoric acid ester groups and the phosphorus atoms are mono- and/or diesterified depending on the selected stoichiometric ratios, and based on polystyrene oxide-block(b)-polyalkylene oxide copolymers which are obtainable starting from a monofunctional starting alcohol by sequential addition of styrene oxide and an alkylene oxide according to the desired sequence and chain length of individual segments, and are subsequently converted to the corresponding phosphoric acid esters, as in the manner described in a), as well as their use as dispersants for pigments and fillers.

EP1167452 describes the use of particular phosphoric acid esters which are based on polystyrene block(b)-polyalkylene oxide copolymers as emulsifiers and dispersants for pigments and fillers.

SUMMARY OF THE INVENTION

The present invention provides shine additives which are effective in a low concentration in a cleaning formulation.

Surprisingly, the Applicant of the present invention has found that the phosphoric acid esters described below can be used as shine additives which are effective in a low concentration in a cleaning formulation.

The present invention therefore provides phosphoric acid esters of general formula 1 or its salt

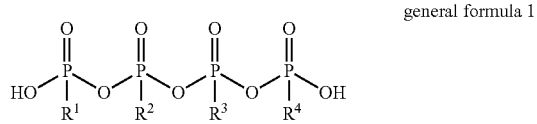

general formula 1 where $R_1$, $R_2$, $R_3$ and $R_4$ are identical or different and are selected from R—O—$(SO)_a$-$(EO)_b$—$(PO)_c$—$(BO)_d$— and OH, where

SO=

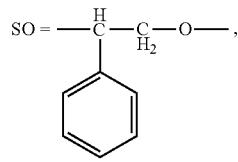

EO=—$CH_2$—$CH_2$—O—,
PO=—$CH(CH_3)$—$CH_2$—O— and
BO=—$CH(CH_2CH_3)$—$CH_2$—O— and with the proviso that at least one of the radicals $R_1$, $R_2$, $R_3$ and $R_4$ is not OH,
and where
a=2.2 to 10,
b=3 to 20,
c=0 to 10,
d=0 to 10, and
R is selected from branched or linear, saturated or unsaturated alkyl radicals having 8 to 20 carbon atoms.

The present invention further provides a process for preparing the phosphoric acid esters according to the invention.

In one embodiment of the present invention, the aforementioned phosphoric acid esters of polyether-modified alkyl alcohols can be used for generating shine on a surface.

In another embodiment of the present invention, the phosphoric acid esters of the present invention bring about a shine effect even in low concentrations.

In yet another embodiment of the present invention, the phosphoric acid esters of the present invention leave behind no greasy or iridescent effect on the surface.

In a further embodiment of the present invention, the phosphoric acid esters of the present invention can be used in hard water.

In yet a further embodiment of the present invention, the phosphoric acid esters of the present invention can reduce spotting on surfaces upon drying of formulations.

In an even further embodiment of the present invention, the phosphoric acid esters of the present invention have a very good stability in aqueous, in particular surface-active, formulations.

In still a further embodiment of the present invention, the phosphoric acid esters of the present invention can be incorporated readily into aqueous formulations without decisively influencing advantageous properties of the aqueous formulations.

DETAILED DESCRIPTION

The phosphoric acid esters according to the invention and formulations which comprise the phosphoric acid esters according to the invention are described below by way of example without intending to limit the invention to these exemplary embodiments. Where ranges, general formulae or compound classes are stated below, then these are intended to encompass not only the corresponding ranges or groups of compounds explicitly mentioned, but also all part ranges and part groups of compounds which can be obtained by removing individual values (ranges) or compounds. Wherever documents are cited within the context of the present description, then their contents should be deemed in their entirety as belonging to the disclosure of the present invention. Within the context of the present invention, wherever compounds, such as e.g. polyethers, are described which can have different units a number of times, then these can be in statistical distribution (statistical oligomer) or arranged (block oligomer) in these compounds. Data relating to number of units in such compounds is to be understood as meaning averages, averaged over all of the corresponding compounds. All of the stated percentages (%) are percentages by mass, unless stated otherwise.

As stated above, the present invention provides phosphoric acid esters of general formula 1 or their salts

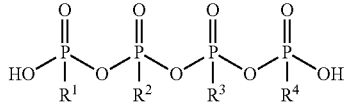

general formula 1 where $R^1$, $R^2$, $R^3$ and $R^4$ are identical or different and are selected from
R—O—$(SO)_a$-$(EO)_b$—$(PO)_c$—$(BO)_d$— and OH, where SO=

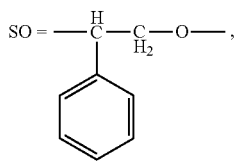

EO=—$CH_2$—$CH_2$—O—,
PO=—$CH(CH_3)$—$CH_2$—O— and
BO=—$CH(CH_2CH_3)$—$CH_2$—O— and
with the proviso, that at least one, preferably at least 2, in particular 3, particularly preferably 4, of the radicals $R^1$, $R^2$, $R^3$ and $R^4$ is not OH, and where
a=2.2 to 10, preferably 2.5 to 7, particularly preferably 3 to 5,
b=3 to 20, preferably 4 to 15, particularly preferably 8 to 12,
c=0 to 10, in particular 0,
d=0 to 10, in particular 0, and
R is selected from branched or linear, saturated or unsaturated alkyl radicals having 8 to 20 carbon atoms, preferably linear, saturated with 8 to 16, in particular 10 to 14, carbon atoms.

Depending on the pH of the surroundings around the phosphoric acid esters according to the invention, the phosphoric acid esters according to the invention can also be present in partially or completely neutralized form as salts. Counterions which may be mentioned in such an embodiment include alkali metal and alkaline earth metal ions, and optionally substituted ammonium ions.

In some embodiments of the present invention, R of formula 1 can be identical or different in the radicals R', $R^2$, $R^3$ and $R^4$.

Phosphoric acid esters preferred according to the invention are characterized in that four, 4, of the radicals $R_1$, $R_2$, $R_3$ and $R_4$ are not equal to OH.

The phosphoric acid esters that are particularly preferred according to the invention are those in which a=2.5 to 5, b=8 to 12 and c=d=0.

Particularly advantageous phosphoric acid esters according to the invention are those in which R is selected from linear, saturated alkyl radicals having 8 to 16, in particular 10 to 14, carbon atoms. Even more preferable phosphoric acid esters are those in which R is a mixture of linear, saturated alkyl radicals having 12 and 14 carbon atoms.

For analyzing a phosphoric acid ester according to the invention and determining the values a, b, c and d, the analytical process described below can be used:

The molar masses of the phosphoric acid esters according to the invention can be determined on an HP 1100 GPC equipped with a column SDV 1000/10000 Angstrom. The mobile phase used is tetrahydrofuran with a flow rate of 1 ml/min. The sample concentration is 10 g/l; detection takes place with an HP RI detector calibrated against polypropylene glycol.

This measurement is combined with an NMR determination (1H, 13C), as a result of which it is possible to determine the individual chain length of a, b, c and d. Particularly in the 1H-NMR, the peak at 4.5 ppm indicates the SO chain length, that around 1.3 ppm the EO chain length and that around 0.8 ppm the length of the alkyl chain. The ester bands of the polyphosphoric acid ester are found in the region around 4.2 ppm.

The polyphosphoric acid with its multiple esterifications can be detected via 31P NMR. In such an instance, the monoesters are seen at 1.5 ppm, the diesters at 1.0 ppm and the tetraesters at 0.0 ppm.

Phosphoric acid esters preferred according to the invention are characterized in that they are not water-soluble. In connection with the present invention, the term "water-soluble" is to be understood as meaning that a substance can dissolve in pure water at 20° C. to a maximum of 1% by weight, preferably 0.5% by weight, particularly preferably 0.1% by weight, with the % by weight referring to the sum of water and tested substance.

The phosphoric acid esters according to the invention can be prepared by processes known to a person skilled in the art. See, for example, the process disclosed in EP0940406. Preferably, the phosphoric acid esters according to the invention are prepared by the process according to the invention described below. Essentially, the process according to the invention comprises alkoxylation steps. Appropriate directions for carrying out alkoxylations can be found by a person skilled in the art in, for example, DE10054462, WO1992012950 and WO2005026273.

The process of the present invention for preparing phosphoric acid esters comprises the process steps
  A) provision of a branched or linear, saturated or unsaturated alkyl alcohol having 8 to 20 carbon atoms or mixtures thereof,
  B) reaction with, based on the alkyl alcohol, 2.2 to 10 mol, preferably 2.5 to 7 mol, particularly preferably 3 to 4 mol, of styrene oxide at a temperature of 80 to 150° C., preferably 100 to 140° C., in particular 110 to 130° C., and a pressure of 0.4 to 1.2 bar, preferably 0.6 to 1 bar, particularly preferably 0.7 to 0.9 bar,
  C) reaction with, based on the alkyl alcohol, 3 to 20 mol, preferably 4 to 15 mol, particularly preferably 8 to 12 mol, of ethylene oxide at a temperature of 80 to 130° C., preferably 100 to 125° C., in particular 110 to 120° C., and a pressure of 0.5 to 6.0 bar, preferably 0.6 to 3.0 bar, particularly preferably 0.8 to 1.5 bar,
  D) reaction with, based on the alkyl alcohol, 0 to 10 mol, preferably 0 mol, of propylene oxide at a temperature of 80 to 130° C., preferably 100 to 125° C., in particular 110 to 120° C., and a pressure of 0.5 to 6.0 bar, preferably 0.6 to 3 bar, particularly preferably 0.8 to 1.5 bar,
  E) reaction with, based on the alkyl alcohol, 0 to 10 mol, preferably 0 mol, of butylene oxide at a temperature of 80 to 130° C., preferably 100 to 125° C., in particular 110 to 120° C., and a pressure of 0.5 to 6.0 bar, preferably 0.6 to 3.0 bar, particularly preferably 0.8 to 1.5 bar, F) reaction with, based on the alkyl alcohol, 0.1 to 1.0 mol, preferably 0.1 to 0.5 mol, particularly preferably 0.2 to 0.3 mol, of polyphosphoric acid $P_4O_{10}$ at a temperature of 50 to 110° C., preferably 60 to 100° C., in particular 70 to 90° C., and a pressure of 0.4 to 1.2 bar, preferably 0.6 to 1 bar, particularly preferably 0.7 to 0.9 bar and optionally H) purification of the resulting phosphoric acid ester.

The process steps D), E) and H) of the process according to the invention are optional; this is expressed in process step D) and E) by the term "reaction with 0 mol" alkylene oxide.

The alcohol provided in process step A) of the process according to the invention is preferably selected from linear, saturated primary alkyl alcohols having 8 to 16, in particular 10 to 14, carbon atoms or mixtures thereof; particularly preferably, the alcohol constitutes a mixture of linear, saturated primary alkyl alcohols having 12 and 14 carbon atoms.

In process steps B to E of the process according to the invention, the alkoxylation takes place in the presence of catalysts, preferably basic (alkaline) catalysts such as alkali metal methanolates, sodium hydroxide and/or potassium hydroxide. Particular preference is given to sodium and potassium methanolate, which are used preferably in an advantageous manner in catalyst amounts of from 0.1 to 5.0% by weight, preferably 0.2 to 0.8% by weight, calculated as solid and based on resulting reaction product. In some embodiments, it is advantageous and therefore preferred to carry out the process according to the invention water-free. The term "water-free" is used in present invention to denote an amount of less than 0.5% by weight of water, based on the total reaction mixture. In other embodiments, it is advantageous to carry out the process according to the invention solvent-free, i.e., without an addition of solvents.

A particularly preferred process according to the invention is characterized in that in process step B) 3 to 4 mol, in process step C) 8 to 12 mol and in process step D) and E) 0 mol—in each case based on the alkyl alcohol—of the particular alkylene oxide are used.

The phosphoric acid esters that can be prepared by the process according to the invention are likewise provided by the present invention.

The phosphoric acid esters that can be prepared by the process according to the invention can constitute mixtures of phosphoric acid esters which, besides the above-described phosphoric acid esters according to the invention of the general formula 1, also comprise those phosphoric acid esters in which at least one of the P—O—P bond has been cleaved.

The present invention further provides a cleaning and/or care formulation comprising phosphoric acid ester of general formula 1a and/or its salts general formula 1a

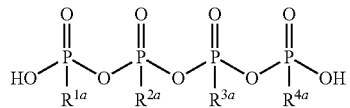

where $R^{1a}$, $R^{2a}$, $R^{3a}$ and $R^{4a}$ are identical or different and are selected from R—O—(SO)$_{aa}$-(EO)$_{bb}$—(PO)$_{cc}$—(BO)$_{dd}$— and OH, where

SO=

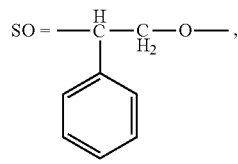

EO=—CH$_2$—CH$_2$—O—,
PO=—CH(CH$_3$)—CH$_2$—O— and
BO=—CH(CH$_2$CH$_3$)—CH$_2$—O— and
with the proviso, that at least one, preferably at least 2, in particular 3, particularly preferably 4, of the radicals $R^{1a}$, $R^{2a}$, $R^{1a}$ and $R^{4a}$ are not OH,
and where
aa=1 to 20, preferably 2.5 to 7, particularly preferably 3 to 4,
bb=1 to 100, preferably 4 to 40, particularly preferably 8 to 12,
cc=0 to 10, in particular 0,
dd=0 to 10, in particular 0, and
R is selected from branched or linear, saturated or unsaturated alkyl radicals having 6 to 24 carbon atoms, preferably linear, saturated with 8 to 20, preferably 9 to 16, in particular 10 to 14, carbon atoms.

It is preferred according to the invention that at least one compound of the general formula 1a is present in an amount of from 0.00001% by weight to 2.5% by weight, particularly preferably from 0.1% by weight to 1.2% by weight, where the % by weight refers to the total formulation, in the aqueous formulation.

Cleaning and care formulations according to the invention are in particular aqueous formulations, where the term aqueous is understood as meaning a water content of at least 30, preferably 80, particularly preferably 98% by weight of water, based on the total formulation.

In some embodiments of the present invention, preference is given to aqueous care and cleaning formulations which, besides the compound of the general formula 1a, comprises at least one surfactant, in which case, for example, anionic, nonanionic, cationic and/or amphoteric surfactants may be present. The total surfactant content of the aqueous formulation is preferably 0.1 to 40% by weight and particularly preferably 0.1 to 12.0% by weight, based on the total formulation.

In some embodiments of the present invention, particularly preferred formulations according to the invention comprise, as phosphoric acid esters of general formula 1a, the phosphoric acid esters according to the invention of the general formula 1 and/or the phosphoric acid esters which can be prepared by the process according to the invention, where preferred embodiments of the aforementioned subjects according to the invention are present in the formulations according to the invention.

The present invention further provides the use of at least one phosphoric acid ester of general formula 1a and/or its salt general formula 1a

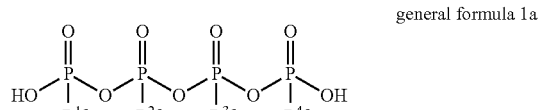

where $R^{1a}$, $R^{2a}$, $R^{3a}$ and $R^{4a}$ are identical or different and are selected from R—O—(SO)$_{aa}$-(EO)$_{bb}$—(PO)$_{cc}$—(BO)$_{dd}$— and OH, where
SO=

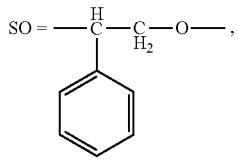

EO=—CH$_2$—CH$_2$—O—,
PO=—CH(CH$_3$)—CH$_2$—O— and
BO=—CH(CH$_2$CH$_3$)—CH$_2$—O— and
with the proviso, that at least one, preferably at least 2, in particular 3, particularly preferably 4, of the radicals $R^{1a}$, $R^{2a}$, $R^{3a}$ and $R^{4a}$ is not OH,
and where
aa=1 to 20, preferably 2.5 to 7, particularly preferably 3 to 4,
bb=1 to 100, preferably 4 to 40, particularly preferably 8 to 12,
cc=0 to 40, preferably 0 to 10, in particular 0,
dd=0 to 20, preferably 0 to 10, in particular 0, and
R is selected from branched or linear, saturated or unsaturated alkyl radicals having 6 to 24 carbon atoms, preferably linear, saturated with 8 to 20, preferably 9 to 16, in particular 10 to 14, carbon atoms, or at least one phosphoric acid ester according to the invention of general formula 1, or a phosphoric acid ester obtainable by the process according to the invention,
or a formulation according to the invention, for generating shine on a surface, preferably on a hard surface which is preferably nonabsorbent.

For the use according to the invention, paper is preferably excluded.

The use according to the invention on surfaces is suitable particularly for vehicles, watercrafts, aeroplanes, window panes and sills, shower dividers, floorings such as carpets, tiles, laminates, parquet, cork flooring, marble, stone and fine stoneware floors, household ceramics such as WCs, wash basins, bidets, shower trays, bathtubs, door handles, fittings, domestic appliances such as washing machines, dryers, dishwashers, sinks made from ceramic or stainless steel, furniture such as tables, chairs, benches, worktops, windows, pots and pans, crockery and cutlery, tools such as surgical instruments, vacuum cleaners, engines, pipelines, tanks and devices for transportation, processing and storage in food processing.

The examples listed below describe the present invention by way of example without there being any intention of limiting the invention, the scope of application of which arises from the entire description and the claims, to the embodiments specified in the examples.

EXAMPLES

Preparation of Phosphoric Acid Esters (According to the Invention)

EX2010/27

591.5 g (3.0 mol) of lauryl/myristyl alcohol and 21.4 g (0.31 mol) of potassium methylate were placed in a reactor and a vacuum was applied. After careful flushing with high-purity nitrogen, the mixture was heated to 115° C. and 1209 g (10 mol) of styrene oxide were added over the course of 15 minutes and under a vacuum of −0.8 bar. After a further 3 hours, the addition of the styrene oxide was complete, detectable from a residual content of styrene oxide which, according to GC, was <0.1% by weight. Then, 1478 g (33.5 mol) of ethylene oxide were metered into the reactor at a rate such that the internal temperature of 120° C. and the pressure of 6 bar were not exceeded. After introducing all of the ethylene oxide, the temperature was kept at 115° C. until a constant manometer pressure indicated the end of the post-reaction. Finally, the unreacted residual monomers were removed in vacuo at 80-90° C. The resulting product was neutralized with the help of phosphoric acid and the water was removed by distillation, and the resulting potassium phosphate by filtration together with a filtration aid. The molecular amount from the determination of the hydroxyl number for an assumed functionality of 1 was M=926 g/mol.

900 g (0.95 mol) of the block polymer were placed in the reactor and, after adding about 50 ml of toluene, heated to 110° C. All of the volatile fractions, in particular any water present in the product, were removed by distillation from the reaction space by applying a vacuum. After aerating with nitrogen, the mixture was heated to 80° C., and 81.2 g of the liquid polyphosphoric acid, 84% strength (0.24 mol of $P_4O_{10}$; Clariant) were added. After 2 hours, the reaction was complete. In the $^1$H-NMR spectrum, aliphatic hydroxyl group was no longer detectable, and in the 31 P-NMR spectrum the still retained polymeric structure was detectable. The more highly polymeric structures are also detectable in the region of 4000 g/mol in the GPC.

Further compounds, as listed in the table below, were prepared in an analogous manner according to the process described above, with adaptation of the correspondingly used amounts.

|  | R | a | B | c | d | x |
|---|---|---|---|---|---|---|
| EX2010/27 | C 12-14 | 3.3 | 10 | 0 | 0 | 0.1-1 |
| EX2010/28 | C 8 | 3.3 | 6 | 0 | 0 | 0.25 |
| EX2010/29 | C 8 | 3.3 | 4 | 0 | 0 | 0.25 |
| AB 215 | C 18.1 | 3.0 | 11 | 0 | 0 | 0.25 |

Preparation of Phosphoric Acid Esters (not According to the Invention)

The Example V3A and V6A from EP 1167452 were reworked as follows:

V3A:

3375 g (23.4 mol) of 1-nonalyl alcohol and 163 g (2.3 mol) of potassium methylate were placed in a reactor. After careful flushing with high-purity nitrogen, the mixture was heated to 110° C. and 3082 g (23.4 mol) of styrene oxide were added over the course of one hour. After a further two hours, the addition of the styrene oxide was complete, detectable from a residual content of styrene oxide which, according to GC, was <0.1% by weight. Then, 9266.4 g (210 mol) of ethylene oxide were metered into the reactor at a rate such that the internal temperature of 120° C. and the pressure of 6 bar were not exceeded. After introducing all of the ethylene oxide, the temperature was held at 115° C. until a constant manometer pressure indicated the end of the post-reaction. Finally, at 80-90° C., the unreacted residual monomers were removed in vacuo. The resulting product was neutralized with the help of phosphoric acid and the water was removed by distillation, the resulting potassium phosphate by filtration together with a filtration aid. The molecular weight from the determination of the hydroxyl number for an assumed functionality of 1 was M=635 g/mol.

635 g of the block polymer (corresponds to 10H equivalent) were charged to the reactor and, after adding about 50 ml of toluene, heated to 110° C. All of the volatile fractions, in particular any water present in the product, were removed by distillation from the reaction space by applying a vacuum. Following aeration with nitrogen, the mixture was heated to 80° C. and 85 g of the liquid polyphosphoric acid, (0.25 mol of $P_4O_{10}$; Merck; content calculated as $P_4O_{10}$: ca. 85%) were added. After two hours the reaction was complete. In the $^1$H-NMR spectrum, aliphatic hydroxyl group was no longer detectable. Here, in the 31P-NMR, polymeric structures were no longer detectable; this was also confirmed in the molecular weight determination in the GPC as described above; no structures above 1000 g/mol were visible. Essentially only monoesters are formed with these reactants.

Compound V6A was prepared analogously.

|     | R   | a   | b | c | d | x    |
|-----|-----|-----|---|---|---|------|
| V3A | C 9 | 1.0 | 9 | 0 | 0 | 0.25 |
| V6A | C 9 | 1.0 | 9 | 3 | 0 | 0.25 |

Shineability

The following formulations were prepared (data in % by weight, pH at 20° C.), wherein:

FAEO stands for fatty alcohol ethoxylate, FAEO C12-18 stands for fatty alcohol $C_{12-18}$ ethoxylate with 8-12 EO, FAEO C6 stands for fatty alcohol $C_6$ ethoxylate with 4-5 EO, APG stands for alkyl polyglucoside; $C_{8-10}$ $G_{1.6}$, MGDA stands for methylglycinediacetic acid (Trilon M).

|            | Form 1A   | Form 1B   | Form 1C   | Form 1D*  | Form 1E*  |
|------------|-----------|-----------|-----------|-----------|-----------|
| FAEO       | 2.0       | 2.0       | 2.0       | 2.0       | 2.0       |
| APG        | 3.0       | 3.0       | 3.0       | 3.0       | 3.0       |
| EX 2010/27 | 0.6       | —         | —         | —         | —         |
| EX 2010/28 |           | 0.6       |           |           |           |
| AB 215     |           |           | 0.6       |           |           |
| V3A        |           |           |           | 0.6       |           |
| V6A        |           |           |           |           | 0.6       |
| MGDA       | 0.1       | 0.1       | 0.1       | 0.1       | 0.1       |
| Water      | remainder | remainder | remainder | remainder | remainder |
| pH         | 7.3       | 7.3       | 7.3       | 7.3       | 7.3       |

|            | Form 2A   | Form 2B   | Form 2C*  | Form 2D*  |
|------------|-----------|-----------|-----------|-----------|
| FAEO C12-18| 2.0       | 2.0       | 2.0       | 2.0       |
| FAEO C6    | 1.5       | 1.5       | 1.5       | 1.5       |
| LAS        | 2.5       | 2.5       | 2.5       | 2.5       |
| EX 2010/27 | 0.6       |           |           |           |
| EX 2010/29 |           | 0.6       |           |           |
| V3A        |           |           | 0.6       |           |
| V6A        |           |           |           | 0.6       |
| Ethanol    | 3.0       | 3.0       | 3.0       | 3.0       |
| Water      | remainder | remainder | remainder | remainder |
| pH         | 11.2      | 11.2      | 11.2      | 11.2      |

For the following test, the formulations were diluted to 1.2% by weight in tap water with 8° dH. (degrees of German hardness) and used.

For a description of the shine increase, equally damaged surfaces are required; these were validated to defined values with a predamaging process. In order to produce targeted damage (shine reduction) on the tile (15×15 cm, Royal Mosa in black), factory-new tiles were damaged in a dishwashing detergent (Neodisher solution (5.7 g/l) at 70° C. for ca. 1 h. The tiles were removed from the immersion bath and rinsed for 5 seconds with distilled water and then dried horizontally for 1 h at 50° C. in a drying cabinet. Before each measurement, the tiles were wiped with ethyl acetate in order to remove dust and other adhering material until residue-free. As a result of this process, the shine was reduced from 94° to a value between 50 and 70° shine. Tiles which produced shine values below 50° were not used for the measurement.

5 ml of test formulation were applied to such a cleaned and pretreated tile using a cleaning cloth (Bodenwunder), which was clamped in a plate measuring 2×5 cm. The cleaner solution was spread in two wiping movements and dried horizontally for at least one hour at room temperature (23° C.). Then, the shine was measured at 5-10 places using a shine measuring instrument (Dr. Lange shine measuring instrument). The numerical values for 60° shine values were determined and noted. Comparison with the values for the damaged, but untreated surface gave the shine increases, noted in the table, after using the corresponding formulation.

The test results are shown in the table below, with Form $1_0$ and Form $2_0$ being formulations without the addition of the phosphoric acid ester (control).

| Formulation | Shine value |
|-------------|-------------|
| Form $1_0$  | 2.7         |
| Form 1A     | 11.9        |
| Form 1B     | 13.3        |
| Form 1C     | 12.7        |
| Form 1D*    | 2.5         |
| Form 1E*    | 2.8         |
| Form $2_0$  | 6           |
| Form 2A     | 14.5        |
| Form 2B     | 13.1        |
| Form 2C*    | 3.2         |
| Form 2D*    | 7.2         |

*not according to the invention

The measurement results show that the formulations according to the invention bring about a significant shine increase compared with the control, whereas those not in accordance with the invention bring about no effect.

The additives not according to the invention result in greasy, streaky or marked, nonuniform surfaces. The additives according to the invention produced an equally shiny area which made the surface also look like new again.

Repair Effect

Scanning electron micrographs were made of the surface of a damaged black tile before and after five-fold application of the formulations Form 2A and Form 2B. The micrographs clearly show the repair effect of the composition according to the invention.

Adhesion Minimization as a Result of Repair Effect

Furthermore, the adhesion on a tile (damaged or undamaged) was measured before and after applying the compositions according to the invention in a vertical and a horizontal measurement arrangement.

The results show that following treatment with the composition according to the invention, the frictional force on the damaged tile is up to 50% less, which is an indication of the repair effect of the composition.

Formulation Examples

Formulation examples are given below in tabular form, including the respective amount, expressed in % by weight, based on the total formulation, using the following raw materials:

TEGOTENS SD 100—Sorbitan sesquioctanoate, Evonik Industries AG
Rewopol D 510 NC—Ethylhexyl sulphate, 40%, Evonik Industries AG Laureth 10, Evonik Industries AG
Rewopol CC 40 B—Cationic/nonionic blend, Evonik Industries AG
Tegotens DO—Decamine oxide, 30%, Evonik Industries AG
Rewocare TS 35—Anionic blend, Evonik Industries AG
Rewoquat CQ 100—Cationic/nonionic blend, Evonik Industries AG
Rewoteric AM KSF 40—Cocoamphodipropionate, 40%, Evonik Industries AG
TEGO Polish Additive WE 50—Emulsion of avocado oil, Evonik Industries AG
TEGO Polish Additive ASL 60—Emulsion of a silicone oil, Evonik Industries AG
Rewopol SC 200—Amphoteric/nonionic blend, Evonik Industries AG
Rewopol SB DO 75—Diisooctyl sulphosuccinate, 75%, Evonik Industries AG
Rewopol NLS 28—Sodium lauryl ether sulphate, 28%, Evonik Industries AG
Rewoteric AM TEG—PEG-2 Tallow fatty betaine, 50%, Evonik Industries AG
Varonic T 202, PEG-2 Tallow amines, Evonik Industries AG
Tegotens EC 11, Terminally capped fatty alcohol, Evonik Industries AG
Rewopol SB FA 30—Laureth-3 sulphosuccinate, 40%, Evonik Industries AG
Rewoteric AM V—C8-10 Amphoacetate, 32%, Evonik Industries AG
TEGO Betaine C 60—Cocamidoproylbetaine, 48%, Evonik Industries AG
VAROX 365—Laurylamine oxide, 30%, Evonik Industries AG

| Bathroom Cleaner | Form-3A | Form-3B | Form-3C |
|---|---|---|---|
| TEGOTENS SD 100 | | | 1.0 |
| Rewopol D 510 NC | | | 1.0 |
| Laureth 10 | | 1.2 | |
| Rewopol CC 40 B | 2.0 | | |
| NaOH | | 0.4 | 2.0 |
| Citric acid | 0.5 | 3.0 | 2.5 |
| Propylene glycol n-butyl ether | 1.0 | | |
| Isopropanol | 5.0 | | |
| EX 2010/27 | 0.6 | 0.6 | 0.6 |
| Water | remainder | remainder | remainder |

| Plastic cleaner | Form-4A | Form-4B | Form-4C |
|---|---|---|---|
| Tegotens DO | 5 | | 3.3 |
| Rewocare TS 35 | | 0.4 | |
| Ethylene glycol | 1 | | |
| Citric acid | 1 | | 1.2 |
| Isopropanol | | 15 | 10 |
| EX 2010/27 | 0.1 | 0.1 | 0.1 |
| Water | remainder | remainder | remainder |

| Paint cleaner and shampoo | Form-5A | Form-5B | Form-5C |
|---|---|---|---|
| Rewoquat CQ 100 | 20 | | |
| Rewoteric AM KSF 40 | 15 | | |
| TEGO Polish Additive WE 50 | | 4 | |
| TEGO Polish Additive ASL 60 | | 1 | |
| Rewopol SC 200 | | | 10 |
| Methylglycinediacetic acid, 40% | | | 6 |
| Tetrapotassium pyrophosphate | 5 | | |
| Citric acid | | | 0.1 |
| Orange terpenes | | | 10 |
| Butyl glycol | | 5 | |
| EX 2010/27 | 0.9 | 0.6 | 0.3 |
| Water | remainder | remainder | remainder |

| Glass cleaner | Form-6A | Form-6B | Form-6C |
|---|---|---|---|
| Tegotens DO | 0.6 | 7.5 | |
| Rewopol SB DO 75 | | 1.0 | |
| Rewopol NLS 28 | | 1.5 | |
| Rewopol TS 35 | | | 1.0 |
| Tegotens SD 100 | | | 0.2 |
| Isopropanol | 15.0 | | 15.0 |
| Methylglycinediacetic acid, 40% | | | 2.0 |
| Sec. alkanesulphonate, 30% | 0.4 | | |
| EX 2010/27 | 0.1 | 0.9 | 0.2 |
| Water | remainder | remainder | remainder |

| WC cleaner | Form-7A | Form-7B | Form-7C |
|---|---|---|---|
| Rewoteric AM TEG | 1.5 | | |
| Rewoquat CQ 100 | 3.0 | | |
| Varonic T 202 | 1.5 | | 5 |
| Tegotens EC 11 | | 1.2 | |
| Tegotens DO | | 2 | |
| Sodium chloride | | | |
| Phosphoric acid | 10 | 5 | |
| Citric acid | | 10 | 8 |
| EX 2010/27 | 0.9 | 0.6 | 0.6 |
| Water | remainder | remainder | remainder |

| All-purpose cleaner | Form-8A | Form-8B | Form-8C |
|---|---|---|---|
| Rewopol SB FA 30 | 12 | | |
| Rewoteric AM V | 8 | | |
| Rewopol SC 200 | | 6 | |
| Tegotens EC 11 | | | 1.2 |
| Tegotens DO | | | 2 |
| REWOPOL NLS 28 | 28.5 | | |
| Undeceth-6 | 2 | | |
| Methylglycinediacetic acid, 40% | | 7.5 | |
| Citric acid | 0.5 | | 10 |
| Phosphoric acid | | | 5 |
| EX 2010/27 | 1.2 | 0.3 | 0.6 |
| Water | remainder | remainder | remainder |

| Dishwashing detergent | Form-9A | Form-9B |
|---|---|---|
| TEGO Betaine C 60 | 4.2 | |
| VAROX 365 | | 11.5 |
| Lauryl ether sulphate, 70% | 20.0 | 18.5 |
| Sodium chloride | 1.3 | 0.8 |
| Citric acid | 0.2 | |
| EX 2010/27 | 1.2 | 1.2 |
| Water | remainder | remainder |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A phosphoric acid ester of general formula 1 or its salt general formula 1

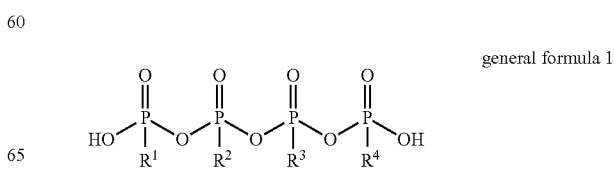

where $R_1$, $R_2$, $R_3$ and $R_4$ are identical or different and are selected from R—O—(SO)$_a$-(EO)$_b$—(PO)$_c$—(BO)$_d$— and OH, where

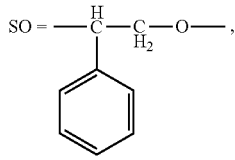

EO=—CH$_2$—CH$_2$—O—,
PO=—CH(CH$_3$)—CH$_2$—O— and
BO=—CH(CH$_2$CH$_3$)—CH$_2$—O— and
with the proviso that at least one of the radicals $R_1$, $R_2$, $R_3$ and $R_4$ is not OH,
where
a=2.2 to 10,
b=3 to 20,
c=0 to 10,
d=0 to 10, and
R is selected from branched or linear, saturated or unsaturated alkyl radicals having 8 to 20 carbon atoms.

2. The phosphoric acid ester or its salt according to claim 1, wherein four of the radicals $R_1$, $R_2$, $R_3$ and $R_4$ are not OH.

3. The phosphoric acid ester or its salt according to claim 1, wherein
a=2.5 to 5
b=8 to 12, and
c=d=0.

4. The phosphoric acid ester or its salt according to claim 1, wherein R is selected from linear, saturated alkyl radicals having 8 to 16 carbon atoms.

5. A process for preparing phosphoric acid esters comprising:
providing a branched or linear, saturated or unsaturated alkyl alcohol having 8 to 20 carbon atoms,
reacting said alkyl alcohol with, based on the alkyl alcohol, 2.2 to 10 mol of styrene oxide at a temperature of 80 to 150° C. and a pressure of 0.4 to 1.2 bar,
reacting a first reaction product of said alkyl alcohol and said styrene oxide with, based on the alkyl alcohol, 3 to 20 mol of ethylene oxide at a temperature of 80 to 130° C. and a pressure of 0.5 to 6.0 bar, and
reacting a second reaction product of said alkyl alcohol, said styrene oxide and said ethylene oxide with, based on the alkyl alcohol, 0.1 to 1.0 mol of polyphosphoric acid $P_4O_{10}$ at a temperature of 50 to 110° C. and a pressure of 0.4 to 1.2 bar.

6. The process according to claim 5, wherein said process is carried out water-free.

7. The process according to claim 5, wherein said process is carried out solvent-free.

8. A phosphoric acid ester prepared by a process according to claim 5.

9. A formulation comprising at least one phosphoric acid ester of general formula 1

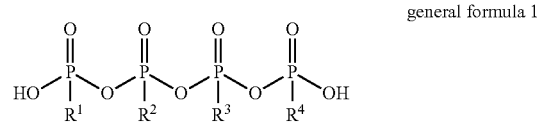

general formula 1 where $R_1$, $R_2$, $R_3$ and $R_4$ are identical or different and are selected from R—O—(SO)$_a$-(EO)$_b$—(PO)$_c$—(BO)$_d$— and OH, where

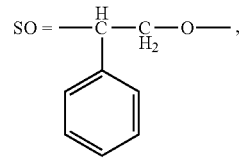

EO=—CH$_2$—CH$_2$—O—,
PO=—CH(CH$_3$)—CH$_2$—O— and
BO=—CH(CH$_2$CH$_3$)—CH$_2$—O— and
with the proviso that at least one of the radicals $R_1$, $R_2$, $R_3$ and $R_4$ is not OH,
where
a=2.2 to 10,
b=3 to 20,
c=0 to 10,
d=0 to 10, and
R is selected from branched or linear, saturated or unsaturated alkyl radicals having 8 to 20 carbon atoms.

* * * * *